(12) United States Patent
Work et al.

(10) Patent No.: US 7,783,072 B2
(45) Date of Patent: Aug. 24, 2010

(54) METHODS AND SYSTEMS FOR CLINICAL TRIAL DATA MANAGEMENT

(75) Inventors: William Work, Claremont, CA (US); Telford Work, Montecito, CA (US); Masashi Ito, Pasadena, CA (US)

(73) Assignee: Therapeias Health Management, LLC, Claremont, CA (US)

( * ) Notice: Subject to any disclaimer, the term of this patent is extended or adjusted under 35 U.S.C. 154(b) by 1126 days.

(21) Appl. No.: 11/380,626

(22) Filed: Apr. 27, 2006

(65) Prior Publication Data

US 2006/0259783 A1 Nov. 16, 2006

Related U.S. Application Data

(60) Provisional application No. 60/675,832, filed on Apr. 27, 2005.

(51) Int. Cl.
*G06K 9/00* (2006.01)
(52) U.S. Cl. .................................................. 382/100
(58) Field of Classification Search ................. 382/100, 382/128
See application file for complete search history.

(56) References Cited

U.S. PATENT DOCUMENTS

| | | | |
|---|---|---|---|
| 5,579,393 A | 11/1996 | Conner et al. | |
| 5,867,821 A | 2/1999 | Ballantyne et al. | |
| 5,912,974 A * | 6/1999 | Holloway et al. | 380/51 |
| 6,141,753 A * | 10/2000 | Zhao et al. | 713/176 |
| 6,496,827 B2 | 12/2002 | Kozam et al. | |
| 6,557,102 B1 | 4/2003 | Wong et al. | |
| 6,587,945 B1 | 7/2003 | Pasieka | |
| 6,804,787 B2 | 10/2004 | Dick | |
| 7,149,784 B2 | 12/2006 | Kitada et al. | |
| 7,523,490 B2 * | 4/2009 | Guo et al. | 726/10 |
| 2002/0010679 A1 | 1/2002 | Felsher | |
| 2002/0049614 A1 | 4/2002 | Rice et al. | |
| 2002/0082480 A1 | 6/2002 | Riff et al. | |
| 2002/0133376 A1 | 9/2002 | Fritschen et al. | |
| 2004/0172286 A1 | 9/2004 | Flood | |
| 2005/0021370 A1 | 1/2005 | Riff et al. | |
| 2005/0027567 A1 | 2/2005 | Taha | |
| 2005/0102158 A1 | 5/2005 | Maeda | |

OTHER PUBLICATIONS

Guidance for Industry E6 Good Clinical Practice: Consolidated Guidance. Apr. 1996. *International Conference on Harmonisation of Technical Requirements for Registration of Pharmaceuticals for Human Use (ICH).* http://www.fda.gov/cder/guidance/959fnl.pdf (accessed Oct. 18, 2006).
International search report dated Oct. 17, 2007 for PCT Application No. PCT/US2006/16366.

* cited by examiner

*Primary Examiner*—Tom Y Lu
(74) *Attorney, Agent, or Firm*—Wilson Sonsini Goodrich & Rosati

(57) ABSTRACT

The invention provides systems and methods for creating certified copies of original information, including original hardcopy documents, in compliance with federal regulations and guidelines. The present invention also provides systems and methods of data management, and in particular, management of such certified copies. In some embodiments the invention relates to original clinical trial information such as source documents, and methods and systems for creating certified copies of such information to create an accessible central repository of such certified copies.

26 Claims, 3 Drawing Sheets

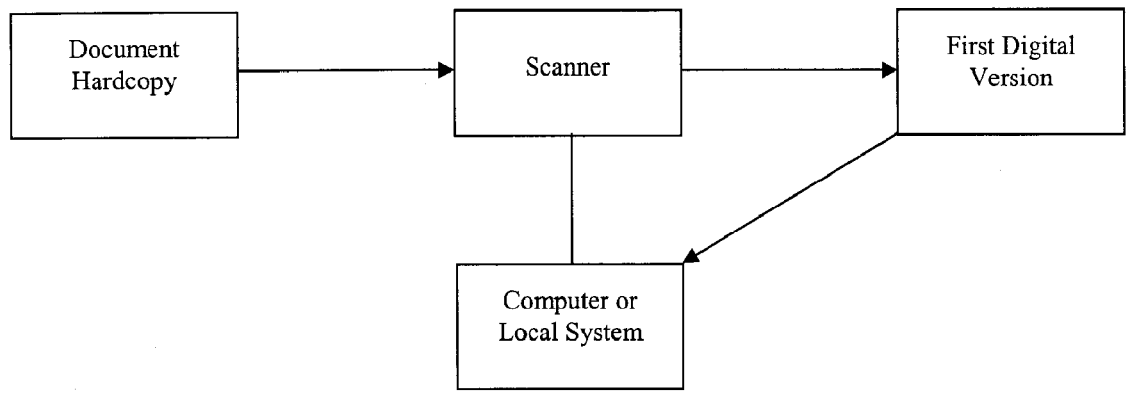
Figure 4
Figure 5
Receipt
| Image or Batch ID: | |
|---|---|
| User ID: | |
| Current Date: | |
| Transmitted Date: | |
| Committed Date: | |
| Image Digital Fingerprint: | |
| Certified Copy Encrypted Signature | |
| External Device Encrypted Signature | |
Figure 6

METHODS AND SYSTEMS FOR CLINICAL TRIAL DATA MANAGEMENT

CROSS-REFERENCE

This application claims the benefit of U.S. Provisional Application No. 60/675,832, filed Apr. 27, 2005, which is incorporated herein by reference in its entirety.

BACKGROUND OF THE INVENTION

Clinical trials are required by the Food and Drug Administration (FDA) in the United States for approval of new therapies, medical devices, biologics, or other interventions to patients. They may be sponsored by a single physician, a small group of physicians, a commercial company, government, or an academic research body. Some trials may have multiple centers, and some may be international.

A source document, as used in clinical trials, is a document in which data collected for the trial is first recorded, or original data. The data contained in a source document is usually later entered in a case report form (CRF) as may be required by the clinical trial protocol. CRFs may be mailed to the sponsor at the conclusion of the clinical trial. Often during a clinical trial, a monitor may check the accuracy and completeness of the source documents, and other trial-related records. The monitor specifically may verify that the data required by the protocol are reported correctly on the CRF. An audit typically occurs at the completion of a clinical trial. An audit is a systematic and independent examination of trial-related activities and documents to determine, at least, whether the data were recorded, analyzed, and accurately reported. An audit includes a comparison of the data originally entered onto a source documents and the data in the CRF to ensure the accuracy of the data entered onto the CRF.

In some instances an auditor or monitor of the clinical trial will physically visit the clinical trial site to view the source documents and/or CRFs to ensure the accuracy of data entered into the CRF. This may be time intensive and costly, particularly when there are multiple centers involved in the clinical trial or when the clinical trial is conducted internationally.

21 C.F.R. Part 11 provides criteria under which the FDA will consider electronic records to be equivalent to paper records, and under which electronic signatures are equivalent to traditional handwritten signatures. Federal guidelines also provide that a certified copy of original information may be created by verifying, by signature, that the copy is an exact copy of the original.

One method of transferring clinical trial data is by facsimile. However, when a document is faxed, the sender does not have a way to certify that the fax received contains the same information that was contained in the original document. Original clinical trial documents may also be physically shipped to a central location and then archived.

Systems and methods are therefore needed that will allow monitors and auditors of a clinical trial to access or view clinical trial documents, including source documents and CRFs, at a centralized location, without the need to ship paper documents, while ensuring the clinical trial data is accurate and reliable. Additionally, systems and methods are required that will comply with the federal rules and guidelines regarding electronic signatures and certified copies of clinical trial documents.

SUMMARY OF THE INVENTION

One embodiment of the invention is a method for providing an electronic certified copy of original information. The method comprises authenticating a user based on a user identification, providing a first digital version of said original information, certifying that a second digital version of said original information is the same as said first digital version, and comparing a first fingerprint of said second digital version with a second fingerprint of said second digital version to ensure they are the same, thereby providing a certified copy of said original information.

In one aspect of the method, the original information is a clinical trial document.

In another aspect of the method, the certified copy resides at a location remote from said user.

In another aspect of the method the user identification is provided by a smartcard.

In another aspect of the method the first digital version is provided by scanning the document.

In another aspect of the method the method further comprises filtering the first digital version of said document, thereby providing the second digital version of the document.

In another aspect of the method the certifying step further comprises re-authenticating said user.

In another aspect of the method the certifying step is accomplished by electronic signature.

In another aspect of the method the first and second fingerprints are checksums.

In another aspect of the method, the method further comprises committing the second digital version of the document when the first and second fingerprints are the same.

Another embodiment of the invention is a method for providing a certified copy of a clinical trial document. The method comprises authenticating a user based on a user identification, providing a first digital version of the clinical trial document by scanning the clinical trial document, committing a second digital version of the clinical trial document, thereby verifying the first and second digital versions are the same, re-authenticating the user, and comparing a first digital fingerprint and a second digital fingerprint of said second digital version to ensure the digital fingerprints are the same, thereby providing a certified copy of a clinical trial document.

In another aspect of the method the certified copy resides at a location remote from said user.

In another aspect of the method the user identification is provided by a smartcard.

In another aspect of the method, the method further comprises filtering the first digital version of the document, thereby providing the second digital version of the document.

Another embodiment of the invention is a computer system for certifying a copy of a document. The computer system comprises computer code that provides a user identification, computer code that authenticates a user based on the user identification, computer code that can provide a first digital version of the document, computer code that allows a user to certify that a second digital version of the document is the same as the first digital version, computer code that compares a first and second fingerprints of the second digital version of the document to detect if the fingerprints are the same, and computer readable medium that store said computer codes.

In one aspect of the system the computer code for authenticating the user based on the user identification and the computer code that compares a first and second fingerprints of the second digital version of the document to detect if the fingerprints are the same are stored on a different computer readable medium than the other the computer codes.

In one aspect of the method, the method further comprises computer code that filters the first digital version of the document thereby providing the second digital version of said document.

In one aspect of the method, the method further comprises computer code that commits the second digital version if the first and second fingerprints are the same.

One embodiment of the invention is a business method for managing electronic medical documents. The method comprises receiving a plurality of electronic medical documents, storing the plurality of electronic medical documents, thereby generating a repository of medical documents, and allowing access to the plurality of electronic medical documents from locations remote from the stored electronic clinical trial documents, thereby managing electronic medical documents.

In one aspect of the method, the plurality of electronic clinical trial documents are certified copies of original clinical trial documents.

INCORPORATION BY REFERENCE

All publications and patent applications mentioned in this specification are herein incorporated by reference in their entirety to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 illustrates converting a paper document into a digital version.

FIG. 5 shows a first digital version of a document filtered to provide a second digital version.

FIG. 6 illustrates the receipt fields that may be included on a receipt sent to a user.

DETAILED DESCRIPTION OF THE INVENTION

Figure 1:
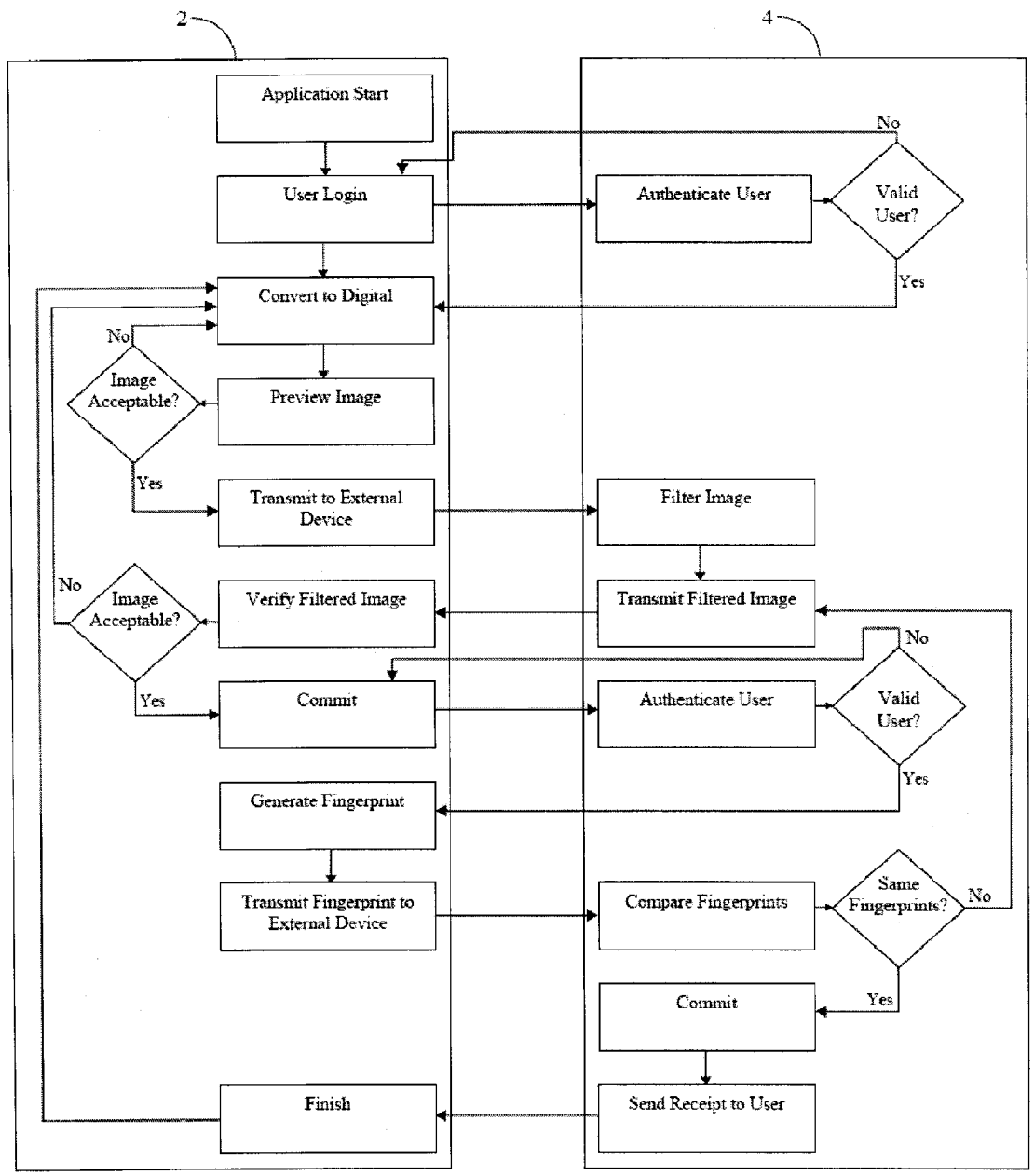
FIG. 1 describes a method of creating a certified copy of a hardcopy of a document.

The invention provides for systems and methods for creating an electronic certified copy of original information. In some embodiments the certified copy is created by verifying, by electronic signature, that the copy is the same as the original information or a digital version of the original information. In preferred embodiments the original information is a clinical trial document, such as a source document. One goal of the present invention is to comply with federal regulations and guidelines for creating certified copies of clinical trial documents using an electronic signature to verify that the copies are the same as the originals. Another goal of the present invention is to create a remote location or repository to store the certified copies and provide for easy access to the copies, as may be required by federal regulations in accordance with clinical trial protocols. While the methods and systems described herein refer to clinical trial documents in particular, it is understood that the invention can and does apply to any type of document, for example without limitation, financial documents, a copy of which may be certified to be an exact copy of the original, wherein such certification is preferably performed by electronic signature.

21 C.F.R. Part 11 provides criteria under which the FDA will consider electronic records to be equivalent to paper records, and under which electronic signatures are equivalent to traditional handwritten signatures. FDA guidance publications, such as Guidance for Industry: Computerized Systems Used in Clinical Trials, 1999 (which can be found at http://www.fda.gov/ora/compliance_ref/bimo/default.html) provide that a certified copy of original information may be created by verifying, by signature, that the copy is an exact copy as the original.

In addition, The International Conference on Harmonisation of Technical Requirements for Registration of Pharmaceuticals for Human Use (ICH) is a project that brings together the regulatory authorities of Europe, Japan and the United States and experts from the pharmaceutical industry in the three regions to discuss scientific and technical aspects of pharmaceutical product registration. The ICH (http://www.ich.org/cache/compo/276-254-1.html) also provides guidelines which can be found at http://www.fda.gov/cder/guidance/959fnl.pdf, in which the definition of source data includes all information in original records and certified copies of the original records.

As used herein, a certified copy of a document includes a copy of original information that has been verified, as indicated by dated signature, as an exact copy having all of the same attributes and information as the original. A certified copy also includes a verified copy of a document that contains substantially the same content, data, or information as the original document. It is also understood that a certified copy may refer to a certified copy of an original paper document (hardcopy), or a certified copy may refer to a certified copy of a digital version of the original paper document. In preferred embodiments, the certified copy as used herein is a certified copy of a digital version of an original paper document, which is a certified copy of the original paper document.

Source documents, or original information, as used herein include, without limitation, hospital records, clinical and office charts, laboratory notes, memoranda, subjects' diaries or evaluation checklists, pharmacy dispensing records, recorded data from automated instruments, copies or transcriptions certified after verification as being accurate and complete, microfiches, photographic negatives, microfilm or magnetic media, x-rays, subject files, and records kept at the pharmacy, at the laboratories, and at medico-technical departments involved in a clinical trial.

Case Report Form (CRF) as used herein includes a document designed to record all of the protocol required information to be reported to the sponsor on each clinical trial subject. CRF includes paper documents as well as those that may be filled out electronically, such as an electronic form, in which case there is no paper document.

Embodiments of the present invention are accomplished by one or more computer readable media, wherein each medium may be configured to include or includes thereon data or computer executable instructions for manipulating data. The computer executable instructions can include data structures, objects, programs, routines, or other program modules that may be accessed by a processing system, such as one associated with a general purpose computer capable of performing various different functions or one associated with a special purpose computer capable of performing a limited number of functions. Computer executable instructions cause the processing system to perform a particular function or group of functions and are examples of program codes for implementing steps for methods disclosed herein. Furthermore, a particular sequence of the executable instructions provides an example of corresponding acts that may be used to implement such steps. Computer readable media includes, without limitation, random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device that is capable of providing data or executable instructions that may be accessed by a processing system.

FIG. 1 illustrates a flow diagram of an exemplary method of providing a certified copy of a document according to the present invention. In general, the method comprises computer or local system 2, and external device 4. As will be described in detail below, a user will start an application on the local system, followed by an initial user login. The login information is transmitted to the external device 4 which authenticates the user. If the user login is valid, the user will convert a hardcopy of a document into a digital version, as may be accomplished in some embodiments with a scanner. The user previews the image to ensure that is it acceptable, or the same, as the hardcopy, then transmits it to the external device, which can be a different computer system such as a server or file storage system. The external device may apply a filtering process to enhance the image quality of the digital version of the document, retains the digital version stored on the external device, and then transmits the digital version back to the user at the local system. The user verifies the image is the same as the digital version sent from the local system, the hardcopy, or both, and if so, commits the data. The user is prompted for an additional authentication which is sent to the external device to reconfirm or reauthenticate the identity of the user. To ensure the committed digital version is the same as the digital version on the external device, digital fingerprints are generated for each digital version and compared. If they are the same, the digital version is further committed. An encryption signature of the committed digital version is created using a user's private key to protect against tampering by others. The committed digital version on the external device may then be sent to a central location or repository where a plurality of certified copies can be kept. An electronic receipt is then sent to the user confirming that the digital version was committed.

In some embodiments the methods of the present invention that are carried out on the local system are performed by a stand alone software application. Such an application can be installed on a computer system via, for example, a CD, or may be downloaded from the internet. In some embodiments the application is built on the Microsoft .NET framework. The embodiments described herein may also be run in a terminal type setting, for example, RDP, ICA, or X-Window, an n-tier type setting, such as a web-based setting, or on the external device, such as a console setting. In other embodiments the components of the present invention may all be included on the same electronic device.

The computer system may be, without limitation, a personal computer, notebook computer, a handheld device such as a personal digital assistant ("PDA") or cellphone, workstation, minicomputer, mainframe, multiprocessor system, network computer, or a processor-based electronic device. The computer system can be any device that can perform the methods of the current invention.

The local or computer system preferably comprises one or more input devices such that a user can interface with the computer system. Exemplary input devices include, without limitation, a keyboard, mouse, trackball, light pen, stylus or other pointing device, microphone, joystick, or voice recognition devices. Any combination of these exemplary input devices may also be used.

Figure 2:
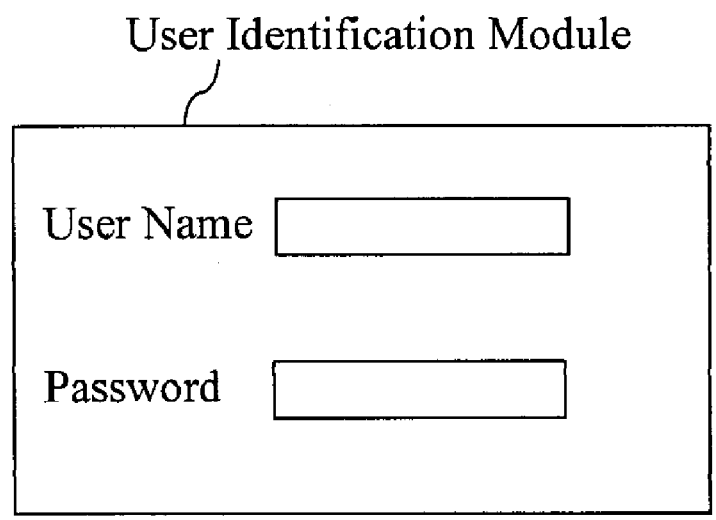
FIG. 2 illustrates a user identification module.

In some embodiments, a user will initiate the application software using a variety of known methods, for example, by double clicking a desktop icon on a computer system using a mouse. First, a user identification module on the local system begins to authenticate the user of the software application. The user identification module may comprise a login screen prompting user entry into fields such as, for example, a username, and a password or passcode. A username and password may be assigned to the user upon account activation, or the user may choose a username and password. Such an exemplary identification module is shown in FIG. 2, providing fields for a user name and password.

In some embodiments asymmetric key cryptography, also known as public-key cryptography, may be used to authenticate a user. Such methods employ a public key and a private key, which are related mathematically. Asymmetric cryptography differs from symmetric cryptography in that in asymmetric cryptography a user does not have to share the private key. A token device, such as a smartcard or an eToken, may be used in such an exemplary public-key cryptography authentication. The use of such token devices and public-key cryptography to authenticate a user are well known in the field, and any such token device available may be used. For example, a user can log on and the user's public key and private key (which remains secret to the user) will encrypt the logon. The encryption is transmitted to the external device, which also houses a copy of the user's public key. The external device can then decrypt the encryption, thereby verifying the user's identity, or authenticating the user.

The public and private key can also be created on the local system without the need to utilize a token device.

The use of smart cards as a way to authenticate a user is well known in the art. Smart cards can be the size of a credit card, and may possess a processor and/or a memory which can exchange data with the computer system. Smart cards may have an embedded Integrated Circuit (IC). The IC may be a logic circuit with its associated memories or a microcontroller with its associated memories and software, or a microcontroller with its associated memories and software coupled to a custom circuit block or interface. In some embodiments, a smart card provides the processor and/or memory in a silicon-based integrated circuit. They also may include electronic or optical interfaces to exchange data with the computer system and may be powered by a battery or other power source.

In some embodiments biometrics can be used to authenticate a user, either by providing the user's private key or both the private key and password. Biometrics includes a method of verifying an individual's identity based on a measurement of an individual's physical feature or repeatable actions where those features and/or actions are both unique to that individual and measurable. Biometrics includes the use of, without limitation, voice, speech, fingerprint, retina, iris, hand geometry, facial recognition, handwritten signature, or veins. In some embodiments the identification module may comprise a biometric recognition, such that the biometric recognition comprises the user's username and passcode. In some embodiments the biometric recognition may comprise the user's username, and then the computer system may prompt the user for a passcode.

In some embodiments the private and public keys and/or username and password may be periodically changed to prevent unauthorized users from gaining access to the local system. A username or public key may also be deactivated, such as if a token device is reported missing or stolen.

Requiring a username and passcode, or public and private key, to authenticate a user complies with the requirements for an electronic signature under 21 C.F.R. Part 11, which states in relevant part that electronic signatures which are not based on biometrics shall employ at least two distinct identification components, such as an identification code and password.

In preferred embodiments a username and password are provided by the user to initially login to the application. The local system then transmits the user-provided username and password to a user authentication module on an external device. The external device may be a computer system, such as a personal computer, or may be a server. In preferred embodiments the external device comprises a database which comprises a plurality of stored usernames and passcodes. The username and passcode may be assigned to a user upon account activation, or when a user first installs the software application.

The computer system may communicate with the external device via a communications link. The communications link may be, for example, a telephone line connection. In other embodiments the communication link may be a wireless connection, a cable modem connection, a satellite connection or a direct connection such as a T1 connection.

The computer system may communicate with the external device using a variety of communication protocols. A set of standardized rules, referred to as a protocol, is utilized to enable computers of other electronic devices to communicate. In some embodiments, the communications protocol used is HTTP ("Hypertext Transfer Protocol"). HTTP is an application-level protocol used in connecting servers and users on the World-Wide Web (WWW). HTTP is based on a request-response mechanism and uses TCP ("Transmission Control Protocol") connections to transfer data. In preferred embodiments HTTPS ("Hypertext Transfer Protocol Secure"), a variant of HTTP that implements the SSL ("Secure Sockets Layer") mechanism, is used. SSL is a standard protocol for implementing cryptography and enabling secure transactions on the Web. SSL uses public key signatures and digital certificates to authenticate a server and user and provides an encrypted connection for the user and server to exchange messages securely. When HTTPS is the protocol used, the URL (Uniform Resource Locator) defining the HTTPS request is directed to a secure port number instead of a default port number to which an HTTP request is directed. Other protocols may be used to transfer data, for example without limitation, FTP or NFS.

The computer system and external device of the present invention may be a part of a network of electronic devices. A network can be a small system that is physically connected by cables or via wireless communication (a local area network or "LAN"). Alternatively, the computer system and external device can be a part of several separate networks that are connected together to form a larger network (a wide area network or "WAN"). Other types of networks of which the computer system and external system may be a part of include the internet, telcom networks, intranets, extranets, wireless networks, and other networks over which electronic, digital and/or analog data may be communicated.

Communication between the computer system and external device may be accomplished wirelessly. Such wireless communication may be bluetooth or RTM technology. In some embodiments a wireless connection is established using exemplary wireless networks such as cellular, satellite, or pager networks, GPRS, or a local data transport system such as Ethernet or token ring over a local area network.

In preferred embodiments the user authentication module then initiates a request to, or queries, a database to detect the transmitted username. If the username exists in the database, the user authentication module queries the database for the passcode or password associated with the username and compares it to the transmitted passcode. If the transmitted passcode is the same as the passcode in the database, the user is successfully authenticated and the software application on the local system will initialize. If the transmitted username is not found in the database or if the transmitted passcode does not match the stored passcode, the software application will not initialize and the user will again be prompted to provide a username and passcode by any of the methods described herein. There may be a limited number of times an authentication may be attempted before the user is locked out of the system. Requiring passcode to authenticate a user helps prevent fraudulent attempts to login under a user's username and also creates a record keeping or tracking system of when a user attempts to login and the identity of the user.

A user as described herein may refer to anybody who is submitting a digital version of a document, or digital data, to an external device for the purpose of creating a certified copy of the document or a digital version of the document. A user may be, without limitation, a nurse, physician, clinician, member of a contract research organization (CRO), or anybody authorized to use the software application and enter clinical trial information, as may be disclosed in a clinical trial protocol.

In preferred embodiments, after the user has been authenticated, the original hardcopy of the clinical trial document (such as a source document) is translated into a digital version of the hardcopy. The digital version can be a file as is commonly found on a personal computer. In preferred embodiments the file is an image file of the hardcopy. Image files may be in any file format that can be transmitted from the local system to an external device, such as, without limitation, TIFF, TIF, JPEG/JPG, GIF, PNG, BMP, PSD, WMF, EMF, PCX, PIC and PDF.

In some embodiments, a scanner is used to create the digital version of the hardcopy. An exemplary scanning step is shown in FIG. 4 where a hardcopy is scanned to provide a first digital version. Scanning a hardcopy of a document to create a digital version of the document is well known in the art, and such scanning devices can be connected to the local computer system in a variety of ways, for example, via a USB or wireless connection. In some embodiments the images are scanned black and white, then compressed with the CCITT group 4 fax encoding algorithm. The scanning may be performed in any other method known in the art, for example, in color, or it may be compressed using a different algorithm.

A scanning device can also be connected to the external device, as may be the case with a network scanner, such that the external device may exercise some degree of control of the generation of the first digital version.

In some embodiments a user may create a digital version of the original paper document and transfer it to the external device via email, either as an individual file or a batch file. The file may then be returned to the user via email or any other method described herein.

In some embodiments the user may create a digital version of the source document without a hardcopy of the source document, as may occur if a user enters clinical trial information directly into an electronic form, as may be found on a computer system. Such a form may be available using a separate software application, or it may be an additional component of the software application disclosed herein. Any method to enter clinical trial information directly onto an electronic device may be employed to generate the digital version in such embodiments.

In preferred embodiments the digital version is temporarily stored on the memory device of the computer system, such as without limitation, a hard drive in the temporary directory, which is protected from access by other users. In preferred embodiments, no temporary files are stored on the local system. Because the data is only temporarily stored in the local computer system, confidential patient information cannot be obtained from the local system, which helps ensure the confidential nature of the clinical trial information.

As used herein, "image" includes, without limitation, multiple images, such as may occur when a plurality of documents are converted to a digital form together, or in a batch. This may occur when there are multiple documents to convert to digital form for a single subject in a clinical trial, or when there are multiple documents to convert from different subjects in a single clinical trial.

In some embodiments the user can preview the image of the document after it is converted into digital form. In general, previewing the digital version includes viewing the digital image to make sure it is acceptable, or the same, as the original hardcopy of the document. In embodiments where a scanner is used to create the digital version of the hardcopy, previewing also allows the user to detect a scan error, such as if part of the hardcopy document was cut off during the scanning process. In some embodiments the user is able to see thumbnail images of the digital document, which can be enlarged by clicking on the image. When documents are scanned as a batch, the user may be able to see thumbnail images of the entire scanned batch, and can similarly view an enlarged version of an image by clicking on it. If the image is acceptable to the user, it can then be transmitted to an external device as described below. However, if it is not acceptable, the document can be scanned and previewed as many times as are necessary until it is acceptable. The preview step helps ensure that the digital version is the same, or contains the same information as, the original hardcopy of the document. When the document is a source document from a clinical trial, this helps ensure the accuracy of the information on the source document after it is converted into digital form. The preview step may be bypassed at the user's request and the procedure can continue as described below.

In preferred embodiments the image or images are transferred to an external device if the digital version is acceptable to the user. The image may be transferred by any of the methods described above. In preferred embodiments the image is transported to the external device using secure transport protocols, such as HTTPS mulitpart form data upload mechanism. In some embodiments secure port number 443 is used to allow the software application to traverse institutional firewalls.

After the image is transferred to the external device, the software application preferably removes the temporary data in the local system memory. The removal ensures that confidential information can't be obtained from the local system and allows all the data to be localized at a central location, described in greater detail below.

If necessary, the external device can then apply a filtering process to the transferred image file, which is interchangeably referred to as post-processing. In some embodiments a filtering process may be used to improve the quality of an image. An exemplary filtering process to improve the quality of the image can include de-speckling, de-skewing, contrast adjustment, noise-reduction, or any other image adjusting technique to render the digital image the same or substantially similar to the hardcopy of the document without altering the content of the image. In other embodiments a filtering process may be used to track when and by whom images are transferred to the external device. Such exemplary filtering processes include without limitation watermarking, time-stamping, or stamping the image with the user's login information. Any combination of the filtering processes described herein, including no filtering process, may be used. In preferred embodiments the image or batch of images is then saved and put on a pending status on the external device, the use of which will be more fully described below. FIG. 5 illustrates an exemplary filtering process wherein a first digital version is filtered to provide a second digital version.

In preferred embodiments, the post-processed image is then transferred back to the local computer system. In some embodiments the images may be sent to the local system as raw HTTPS binary data. In preferred embodiments, the images are transferred with an identifier associated with the image stored on the external device which will assist in identifying the image or images later in the process. In embodiments where a batch of images is transferred, there is an identifier transferred for the entire batch.

In preferred embodiments, the user then views the images sent from the external device for verification by the user. The verification ensures that the images sent from the external device contain the same data or content as both the original hardcopy and the digital version the user initially sent to the external device. The user can view the images using the same interface used to preview the images described above, or the interface may be a separate verification interface. If the image is acceptable, or rather, if the image is the same as, or substantially the same as, the hardcopy and first digital version, the user verifies the image. The verification can occur by the user clicking on a button on the interface, or by any other method in which a user may interface with the local computer system.

When the user verifies, or certifies, that the image received from the external system is the same as the first digital version, the user is "committing" the data, or rather, the second digital version. Verifying, certifying, and committing may be used interchangeably herein. In some embodiments, committing data comprises a saving action, which creates or modifies, or an action which deletes, an electronic record or portion of an electronic record. An example is, without limitation, pressing a key of a keyboard that causes information to be saved to durable medium.

Figure 3:
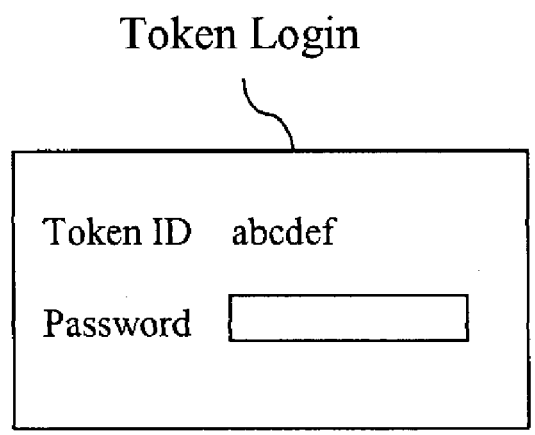
FIG. 3 illustrate the use of a token device to identify the user.

When the user certifies, or commits, the data, the user will again be prompted by a user identification module on the local system to authenticate the identity of the user. The user identification module may be the same as the module described above, for example without limitation, a login screen requiring a username or password, or it may be an interface requiring a token device such as an eToken or a smartcard. In preferred embodiments, a token device is used, and an authentication step as described above using asymmetric key-cryptography, or public-key cryptography, is used. FIG. 3 shows an exemplary token login in which a user logs in to the token device. As described above, a private key encrypts the logon and the public key which is also housed on the external device decrypts the information, thus re-authenticating the identity of the user. If the user is authenticated, the process continues as described below, but if not, the user is again prompted to logon until a match occurs. There may be a limit on the number of unsuccessful login attempts before the user is locked out of the application software.

By requiring the user to again provide login information during or after the committing step, the system is in accordance with federal guidelines for preventing a third party from physically taking over a user's session on the local computer system, and also creates a two-part authentication system. In some embodiments, a biometric authentication may also occur during or before the committing step, such as a required fingerprint or other biometric as disclosed herein. A biometric aspect to the authentication at the committing step would create a three-part authentication.

As will be detailed below, in preferred embodiments using public/private keys to authenticate the user during the committing step, the private key associated with the user is used in creating a signature of the certified copy stored either on the external device or central repository of certified copies.

The next step in the method of generating a certified copy is to compare the image that is pending on the external device (as described above) with the image committed, or verified, by the user. Because the user has committed the image or other file, the external device must compare the committed image to the image on the external device to ensure the images are the same. This step is performed to ensure that the image which the user has verified is the same as the image stored on the external device. By ensuring the two images or batch of images are the same, this ensures that the images or batch of images that was committed is the same as the image or batch stored on the external device. This helps certify that the images committed contain the same data, content, or information that is contained in the images stored on the external device, further in compliance with FDA standards for creating a certified copy.

In preferred embodiments the comparison is accomplished by comparing digital fingerprints of the images. Digital fingerprints can be used to determine if a change has been made to, for example, an image file, by comparing the fingerprint of the image file before and after, for example, a transmission of the image. As used herein, a digital fingerprint is synonymous with a message digest. A digital fingerprint includes the output from any type of cryptographic algorithm, and includes, without limitation, a checksum, hash sum or hash value. Comparing the digital fingerprints is preferably performed by comparing checksums of the different images or batch of images. In some embodiments the checksum is an MD5 checksum.

Hash functions include without limitation, MD (including MD5), SHA (including SHA-256), RIPEMD (including RIPEMD-160), and WHIRLPOOL. Any other hash sum known in the art may be used as a fingerprint.

In some embodiments, when the user commits the image or batch of images as described herein, the local system computes a checksum on the committed image and transfers the computed checksum as well as the identifier associated with the images or image batch which was initially sent to the local system from the external device when the image was sent to the local system after the filtering process. Thus, the commit request by the user is sent along with the checksum of the committed image and image batch identifier. In some embodiments the checksum is generated and transmitted to the external device after the user is authenticated by the authentication module on the external device.

The pending image or images are at this step already stored on the external device, and thus the committed images do not need to be retransmitted from the local system to the external device. All that is required is a comparison of the fingerprint generated from the committed image (which is preferably generated by the local system) with a fingerprint generated of the pending image on the external device. The external device thus creates a fingerprint on the stored pending image, and compares it to the fingerprint transmitted from the local system with the commit request. This ensures that the image which has been committed by the user is the same as the image stored on the external device, ensuring compliance with federal regulations and guidelines described herein.

If the two fingerprints are the same, the image which was pending on the external device is deemed to be the same as the image committed by the user, and thus certified by the user to be an exact duplicate of the first digital version of the document, and therefore an exact copy of the original hardcopy. Thus, by authenticating the user as described herein, and further ensuring the digital fingerprints of the two documents are the same, a certified copy is created which is verified by electronic signature, in compliance with federal standards and guidelines for documents in a clinical trial. If the digital fingerprints are the same, the image on the external device is committed as the certified copy of the clinical trial document, and can be saved on the external device, or may be transmitted to another device or location, which may be an additional storage device. In preferred embodiments, the image files are stored in a database, in binary large object (BLOB) fields. If the digital fingerprints are not the same, or do not match, the external device will retransmit the filtered or post-processed image for verification as described above, and the procedure will be repeated in an attempt to create a certified copy.

In some embodiments the image located on the external device which has been "committed" will contain an indication that is has been committed, by electronic signature, that the image is the same as the original document or the original digital version of the document which has been created by the user. For example, the image may contain a stamp with the username to indicate by whom it was certified. In some embodiments a separate unique identifier which is stored in the external device and associated with the user may be printed or stamped on the image rather than the username. This may be required if the username or private key must remain anonymous for security reasons. Other indications may contain a time and/or date stamp, to indicate when it was committed. A digital fingerprint may also be indicated on the image to indicate the fingerprint computed for the image at the time of certification. Such indications may assist in creating a tracking system for any changes that may be subsequently made to an image. For example, if an image is later accessed, a tracking requirement may generate a digital fingerprint and stamp it on the image to indicate the image was accessed and perhaps altered. When an image is later accessed, other indications are preferably indicated on the image as well, for example, a user identifier and/or time and date stamps to indicate when and by whom the image was accessed, and perhaps, edited.

In preferred embodiments, once the user has committed the image and the digital fingerprints and compared and determined to be the same, the digital fingerprint of the image or batch of images is stored in the external device, associated with the image identifier discussed above, a user identification which indicates the identity of the user, and a date and time stamp indicating when the image was committed. Storing these values helps keep a record of the identity of the user who committed the image and when it was committed, as well as the digital fingerprint of the image.

In preferred embodiments, once the image is committed as described above, the user's private key is used to generate a signature of the image. The signature of the image may be created using symmetric-key algorithms, which utilize the same shared secret key for encryption and decryption. The signature is preferably created with public key cryptography, or asymmetric key cryptography, as described herein. In other embodiments the external device may also generate an additional signature using its own private key. This would provide an additional guarantee the image files are not altered and as a way to safeguard against tampering by the user. The signature or signatures are then preferably stored with the committed digital version. In some embodiments the signature is an MD5/RSA algorithm signature.

The signature of the image is preferably stored in the external device or other storage device, and is associated with the image or image batch identifier, user identification which indicates the identity of the user, and a date and time stamp indicating when the image was committed, as well as the digital fingerprint of the image.

The external device then preferably issues a digital receipt to the user. The receipt may include the image identifier, user identification to identify the committing user, the time and date stamp when the image was committed, and preferably the digital fingerprint of the committed image, as well as the signature of the image. The digital receipt may include any information necessary to identify the user that committed the image, when it was committed, and the encrypted signature of the image. The receipts may be sent via email, or may be sent to the user in HTTP format so that a user can view the receipt on a web browser. FIG. 6 illustrates exemplary fields that may be included in the receipt.

Once the image is committed and removed from pending status, the image can then be sent to a storage location or repository, of certified copies of clinical trial documents. It is one purpose of the present invention to create a central location for storage of certified copies of clinical trial documents. The systems and methods of this invention therefore provide a business model or method for creating a central location of certified copies of clinical trial documents which may be accessed as described below. A distributed network of certified copies of clinical trial documents may also exist according to the present invention.

Auditors or monitors can then access and view the certified copies of the clinical trial documents, such as source documents, and compare them to the information submitted from the clinical trial in the CRF. The invention therefore provides a streamlined system for auditors and monitors to compare the original documents on which clinical trial information is recorded with the CRF or multiple CRFs submitted with the clinical trial in compliance with federal regulations. Auditors includes FDA auditors as well as sponsor auditors, or any other body or organization, or employees of such groups, that might need to access source documents or certified copies of source documents. Auditors, for example, may be given access to view such certified copies using, for example, a web site from which they can view the images stored on the repository or central location.

While limited viewing-only access may be given to some entities or individuals, access is preferably given to users to allow them to change or edit data, content, or information on certified copies of clinical trial documents that are stored at the central location or repository. This allows for errors made on the original source document, a copy of which has already been certified, to be corrected and saved as a new image which is associated with the original digital image so that an auditor, for example, would be able to access both images and view the change made to the data. For example, a blood pressure that was incorrectly written down on a source document for may be corrected by a user and saved as a second image.

To allow users to make these changes to the data on certified copies of source documents, the central repository preferably stores not only an image file of the digital version of the document, but also a file comprised only of data from the source document which can be manipulated or changed. Such a data file may be created when the first digital version of the hardcopy is initially sent to the external device. For example, a user wishing to change a blood pressure reading on a certified copy may log on to the computer system and enter an image or batch identifier to indicate to the repository which batch of image should be displayed. The repository will then display the image file as well as the data file containing the content of the image file to the user. The user can then manipulate the data in the data file and submit the changes. As data files may also be stored in the central repository, it is then necessary to compare digital fingerprints of the data file similarly to the image files as described above. Likewise, a signature is generated from the data file using, preferably, public key cryptography, and will be sent to the user in the receipt as is the signature on an image file.

When such changes are made to a certified copy, the user identification, image or batch identifier, time and date stamp are again transmitted to the external device and ultimate the central repository as described above. The new, or second image, is preferably associated with the original certified copy so that an auditor, for example, can view all the images that have been created or modified by a user, and have access to when and by whom such changes were made. This allows a user to change the data in a source document while providing a record or trail of what changes may have been made to a source document.

Attempting to access stored images can, for example, visit a web page which can display the images using, for example, embedded HTTP. It may also be desirable for clinicians, including physicians and nurses, to access the images of the clinical trial documents after they have been committed to, for example, make changes to them. A clinician could login using the software as described herein, and could gain access to the images to make any necessary changes. Such changes are preferably tracked using any of the tracking methods described herein.

Such a repository, or storage device, can be a location for data management of clinical trial documents. A plurality of pharmaceutical companies with multiple ongoing clinical trials, can, for example, provide certified copies of their original documents and CRFs to the centralized data management repository using methods and systems described herein. A centralized location for certified copies of original documents and/or CRFs would allow monitors and auditors, as well as clinicians, to easily access the images of the certified copies and/or CRF to, for example, compare the information contained in each as may be required by the clinical trial protocol. This would eliminate both the need for a visit to the clinical trial site as well as physical shipments of the paper documents to a central location. This would streamline the process for monitoring and/or auditing multiple clinical trials by a plurality of sponsors.

While the systems and methods described herein have primarily been described in relation to clinical trial documents, the invention may also be used in, or a component of, an electronic health record system. For example, it may be beneficial for health organizations to use certified copies of their paper charts rather than to simply scan them. This may be especially important as they convert their paper records into electronic format.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for providing an electronic certified copy of original information, comprising:
    authenticating a user of a computer system based on a user identification;
    said user providing a first digital version of said original information to a remote location;
    said user certifying that a second digital version of said original information is the same as said first digital version;
    and comparing a first fingerprint of said second digital version with a second fingerprint of said second digital version to ensure said first and second fingerprints are the same, thereby providing an electronic certified copy of said original information.

2. The method of claim 1, wherein said original information comprises original clinical trial data.

3. The method of claim 1, wherein said certified copy resides at a location remote from said user.

4. The method of claim 1, wherein said first digital version is provided by scanning said original information.

5. The method of claim 1, further comprising filtering said first digital version of said original information, thereby providing said second digital version of said original information.

6. The method of claim 1, further comprising re-authenticating said user after said certifying step, wherein said re-authentication comprises said user providing a token to said computer system.

7. The method of claim 1, wherein said certifying step is accomplished by electronic signature.

8. The method of claim 1, wherein said first and second fingerprints are checksums of said second digital version.

9. The method of claim 1, further comprising committing said second digital version of said original information when said first and second fingerprints are the same.

10. The method of claim 1, further comprising transmitting a receipt to said user after comparing said first and second digital fingerprints, wherein said receipt comprises at least one encrypted signature of said certified copy.

11. A method for providing a certified copy of a clinical trial document, comprising:
    authenticating a user of a computer system based on a user identification;
    said user providing a first digital version of said clinical trial document to a remote location by scanning said clinical trial document;
    said user verifying said first and a second digital version of said clinical trial document are the same;
    re-authenticating said user;
    comparing a first digital fingerprint and a second digital fingerprint of said second digital version to ensure said digital fingerprints are the same, thereby providing a certified copy of said clinical trial document.

12. The method of claim 11, wherein said certified copy resides at a location remote from said user.

13. The method of claim 11, wherein said re-authenticating said user comprises said user providing a token to said computer system.

14. The method of claim 11, further comprising filtering said first digital version of said document, thereby providing said second digital version of said document.

15. The method of claim 11, further comprising transmitting a receipt to said user after comparing said first and second digital fingerprints, wherein said receipt comprises at least one encrypted signature of said certified copy.

16. A computer system for certifying a copy of a document, comprising:
    computer code for providing a user identification;
    computer code that authenticates a user based on said user identification;
    computer code that provides a first digital version of said document;
    computer code that allows said user to provide said first digital version of said document to a remote location;
    computer code that allows a user to certify that a second digital version of said document is the same as said first digital version;
    computer code that compares a first fingerprint and a second fingerprint of said second digital version of said document to detect if said fingerprints are the same; and
    computer readable medium that store said computer codes.

17. The computer system of claim 16, wherein said computer code for authenticating said user based on said user identification and said computer code that compares a first and second fingerprints of said second digital version of said document to detect if the fingerprints are the same are stored on a different computer readable medium than the other said computer codes.

18. The method of claim 16, further comprising computer code that filters said first digital version of said document thereby providing said second digital version of said document.

19. The computer system of claim 16, further comprising computer code that commits said second digital version if said first and second fingerprints are the same.

20. The method of claim 1, wherein said second digital version of said plurality of said original information is provided from a remote location.

21. The method of claim 1, wherein said first fingerprint of said second digital version is provided from a remote location.

22. The method of claim 1, wherein the comparing of said first fingerprint of said second digital version with said second fingerprint of said second digital version is performed at a remote location.

23. The method of claim 5, wherein filtering comprises de-speckling, de-skewing, contrast adjustment, noise-reduction, watermarking, time-stamping, or stamping the image with the user's login information.

24. The method of claim 5, wherein filtering is performed at a remote location.

25. The method of claim 11, wherein the comparing of said first fingerprint with said second fingerprint of said second digital version is performed to a remote location.

26. The method of claim 1 or 11, wherein said certified copy is sent to a repository for storage.

* * * * *